(12) United States Patent
Li

(10) Patent No.: US 6,812,342 B2
(45) Date of Patent: Nov. 2, 2004

(54) ESTERS OF CYCLIC ADP RIBOSE DERIVATIVES

(75) Inventor: Wen Hong Li, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/176,359

(22) Filed: Jun. 20, 2002

(65) Prior Publication Data

US 2003/0013869 A1 Jan. 16, 2003

Related U.S. Application Data

(60) Provisional application No. 60/299,556, filed on Jun. 20, 2001.

(51) Int. Cl.[7] .................. C07H 19/11; C07H 19/04; C07H 19/20
(52) U.S. Cl. ............. 536/26.11; 536/26.2; 536/26.21; 536/26.22; 536/26.23; 536/26.71; 536/123.13; 536/124; 536/127
(58) Field of Search .................. 536/26.23, 25.6, 536/26.2, 26.21, 26.22, 26.71, 123.13, 124, 26.11, 26.12, 127

(56) References Cited

U.S. PATENT DOCUMENTS

| | | |
|---|---|---|
| 5,393,667 A | 2/1995 | Strumwasser et al. ...... 435/200 |
| 5,486,604 A | 1/1996 | Walseth et al. .......... 536/26.13 |
| 5,608,047 A | 3/1997 | Sih .......................... 536/26.26 |
| 5,834,436 A | 11/1998 | Tsien et al. .................... 514/23 |
| 5,866,548 A | 2/1999 | Tsien et al. .................... 514/23 |
| 5,872,243 A | 2/1999 | Gee et al. ................ 536/26.23 |
| 5,955,453 A | 9/1999 | Tsien et al. ................. 514/103 |
| 5,980,862 A | 11/1999 | Meade et al. .............. 424/9.35 |

Primary Examiner—James O. Wilson
Assistant Examiner—Ganapathy Krishnan
(74) Attorney, Agent, or Firm—Gardere Wynne Sewell LLP

(57) ABSTRACT

The present invention is directed to the field of organic chemistry in general and specifically to the preparation of hydrophobic derivatives of cyclic ADP ribose. One form of the present invention is the composition of one or more hydrophobic derivatives of cyclic ADP ribose. In another form of the present invention, a method for preparing a hydrophobic composition is described. Compositions of the present invention are useful for the study of in vivo calcium metabolism.

11 Claims, 7 Drawing Sheets

ESTERS OF CYCLIC ADP RIBOSE DERIVATIVES

This application claims priority from U.S. Provisional Patent Application Ser. No. 60/299,556, filed Jun. 20, 2001.

FIELD OF THE INVENTION

The present invention is directed to the field of organic chemistry in general and specifically to the preparation of hydrophobic derivatives of cyclic ADP ribose.

BACKGROUND OF THE INVENTION

Intracellular calcium plays key roles in stimulation-secretion coupling in pancreatic islet β-cells. The elevation of cellular cytosolic calcium concentration ($[Ca^{2+}]_c$) is mediated through two pathways: $Ca^{2+}$ release from intracellular calcium stores and $Ca^{2+}$ influx from extracellular medium. The mechanisms underlying internal calcium release in β-cells remain incompletely understood, and the relative contribution of intracellular $Ca^{2+}$ release to the overall $[Ca^{2+}]_c$ increase and subsequent insulin secretion needs to be determined.

$Ca^{2+}$ release from intracellular stores is an important signaling mechanism for a variety of cellular processes and is generally controlled by two systems, the $IP_3$ and cADPR systems (FIG. 1). $IP_3$ acts directly on the $IP_3$ receptor (IP3R) localized in the endoplasmic reticulum (ER). IP3R forms the $Ca^{2+}$ releasing channel and regulates the efflux of $Ca^{2+}$ from the ER to the cytosol. Cyclic ADP ribose increases the opening probability of other intracellular $Ca^{2+}$ releasing channel formed by the ryanodine receptor (RyR) in the ER.

$Ca^{2+}$ influx through voltage gated $Ca^{2+}$ channels is a well-characterized phenomenon in β-cells, and it is thought to play an important role in maintaining $Ca^{2+}$ homeostasis, especially during glucose stimulation. However, contributions from internal calcium release cannot be ignored. $Ca^{2+}$ influx from extracellular sources and $Ca^{2+}$ release from the intracellular pool in human β-cells has been examined, and showed that 42–75% of the increase in intracellular $Ca^{2+}$ by glucose stimulation was due to the release of $Ca^{2+}$ from the intracellular stores. Both $IP_3$ and cADPR signaling systems have been reported in insulin secreting β-cells, but controversies remain regarding which system is more important for maintaining proper insulin secretion responses.

To examine $IP_3$ or cADPR induced $Ca^{2+}$ release in β-cells, it is necessary to deliver these second messengers inside cells and assay their effects on cellular calcium homeostasis and insulin secretion. Methods relying on triggering cell surface receptors to produce endogenous $IP_3$ or cADPR inevitably activating other signaling pathways, making it impossible to separate the effects caused by $IP_3$ or cADPR from those caused by other signaling branches. To deliver exogenous $IP_3$ or cADPR inside cells, one need to overcome the difficulty of getting them across cell membranes. Both $IP_3$ and cADPR are charged and hydrophilic molecules at physiological pH, thus are membrane impermeant. Previous techniques of getting these two molecules across hydrophobic cell membranes include microinjection, patch clamping, electroporation or detergent assisted permeabilization. All these methods are invasive and suffer from major drawbacks such as disrupting intact cell membranes, letting cytosolic factors leak out of cells, and compromising long term viability of cells. In addition, techniques such as microinjection or patch clamping can only be applied to single cells, making it practically impossible to study more physiological preparations such as islets.

SUMMARY OF THE INVENTION

One form of the present invention is a hydrophobic compound of the general formula:

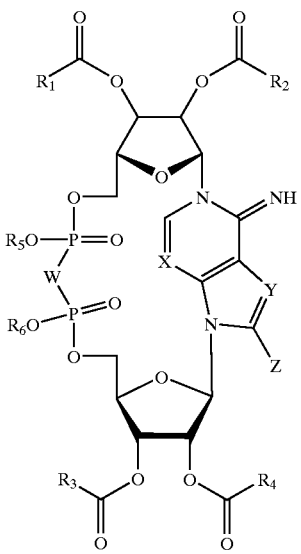

where $R_1$, $R_2$, $R_3$ and $R_4$ are each independently hydrogen or linear or branched alkyl groups having from 1 to 12 carbon atoms. $R_5$ and $R_6$ are each an alkyl group, metallic cation, a photo-labile caging group, or an acyloxymethylgroup or a homologue thereof. W is $CH_2$, $CF_2$, or CHF. X is N or CH. Y is N or CH. Z is chosen from the group including H, Br, $NH_2$, $OCH_3$, $CH_3$ and $N_3$.

Another form of the invention is a method for preparing a hydrophobic composition comprising the following steps:

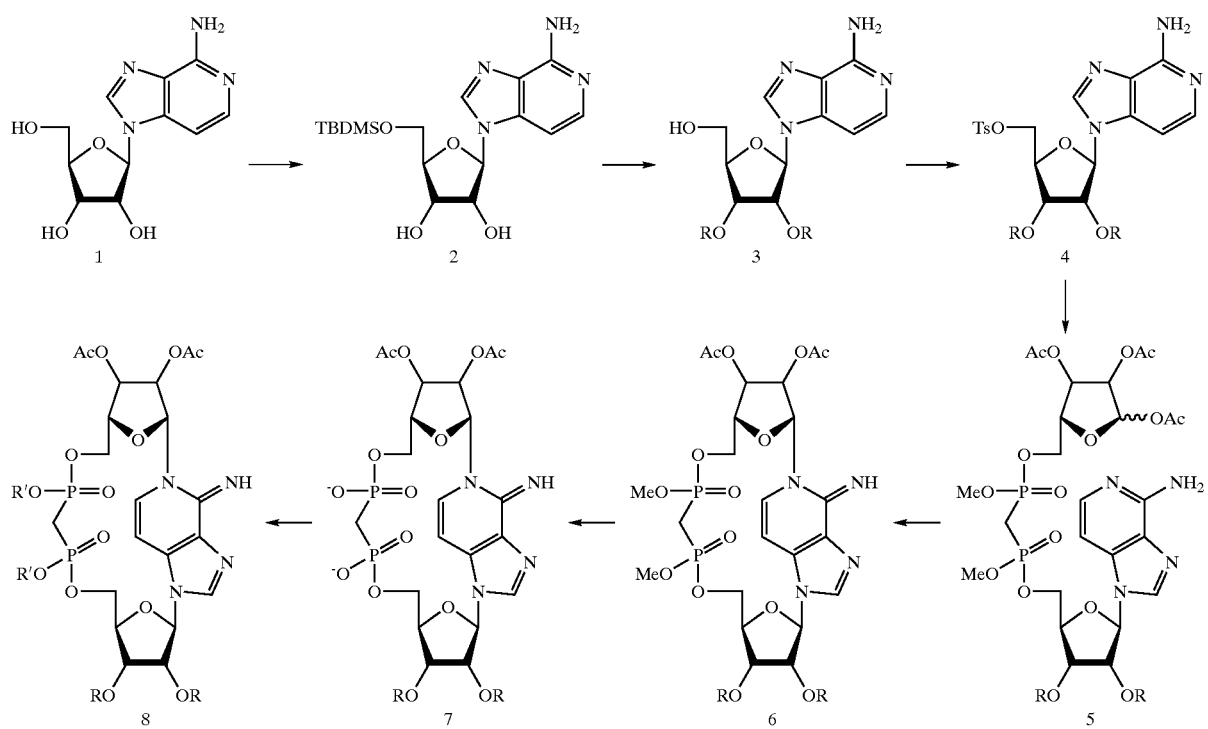

where RO and R'O comprise independently in each location carboxylate groups further comprising from 2 to 20 carbon atoms.

BRIEF DESCRIPTION OF THE FIGURE

The above and further advantages of the invention may be better understood by referring to the following detailed description in conjunction with the accompanying drawings in which corresponding numerals in the different FIGURES refer to the corresponding parts in which.

DETAILED DESCRIPTION OF THE INVENTION

Figure 1:
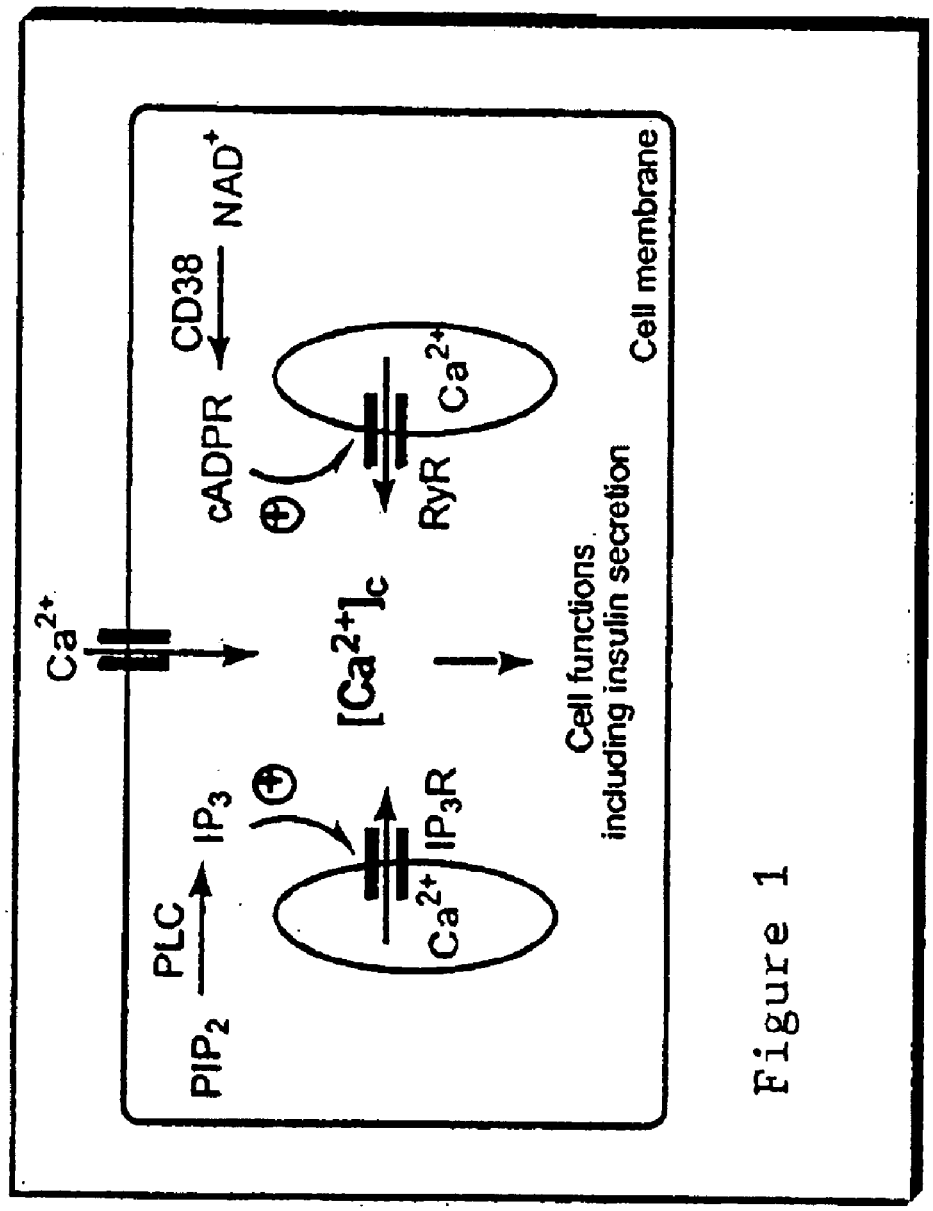
FIG. 1 depicts aspects of calcium metabolism in accordance with the present invention.

While the making and using of various embodiments of the present invention are discussed herein in terms of organic chemistry, it should be appreciated that the present invention provides many inventive concepts that may be embodied in a wide variety of specific contexts. The specific embodiments discussed herein are merely illustrative of ways to make and use the invention are not meant to limit the scope of the present invention in any way.

Terms used herein have meanings as commonly understood by a person of ordinary skill in the areas relevant to the present invention. Terms such as "a," "an," and "the" are not intended to refer to only a singular entity, but include the general class of which a specific example may be used for illustration. The terminology herein is used to describe specific embodiments of the invention, but their usage does not limit the invention, except as outlined in the claims.

Novel techniques to prepare hydrophobic derivatives of phosphate-containing molecules including cADPR have been developed. These hydrophobic derivatives are expected to diffuse across cell membranes of fully intact cells and regenerate their parent molecules by cellular esterase hydrolysis. Photo-chemical uncaging techniques may also be used to activate these molecules with desired temporal and spatial precision. A "caged" molecule is masked by a photo-labile protecting group, and is thus biologically inactive. Photolysis with a flash of UV light ("uncaging") removes the photo-labile protecting group to restore the biological activity of the molecule abruptly. Caged and hydrophobic derivatives of cADPR serve as powerful pharmacological tools for the to study of their roles in cellular $Ca^{2+}$ signaling, and allow the assay of their effects on insulin secretion in intact cell populations.

A natural metabolite, cADPR, has been purified from sea urchin egg homogenates and was found to have $Ca^{2+}$-mobilizing activities. Cyclic ADP ribose showed distinct $Ca^{2+}$ releasing properties from ones caused by $IP_3$. Pharmacological studies suggested that cADPR mediates $Ca^{2+}$ release through ryanadine receptor (RyR), one of the two major intracellular $Ca^{2+}$ releasing channels (the other is IP3R). Cyclic ADP ribose has been shown to be able to release $Ca^{2+}$ from intracellular stores in a number of mammalian cells.

Cyclic ADP ribose is formed in one step from $NAD^+$, a common reduction-oxidation cofactor. The reaction is catalyzed by an enzyme, ADP ribosyl cyclase, that was first purified, sequenced, and cloned from the ovotestis of the marine mollusk Aplysia. The enzyme activity was also found to be present in many, if not most, mammalian tissues. Considerable homology (69%) of the amino acid sequence between Aplysia ADP-ribosyl cyclase and human lymphocyte surface antigen CD38 has been observed. Subsequent studies from a number of laboratories showed that CD38 from human, mouse, and rat possess ADP-ribosyl cyclase activity, synthesizing cADPR from $NAD^+$. CD38 has also been found to exist in many animal tissues, and in both plasma membrane and microsomal membrane fractions.

There have been a number of discrepancies regarding the signaling role of cyclic ADP ribose. The mechanism of how cADPR activates ryanadine receptors is not fully understood at the moment, but it appears that cADPR requires the presence of other proteins such as calmodulin to exhibit its biological activity. The lack of $Ca^{2+}$ responses to cADPR using permeabilized cells, microinjection or patch clamping technique may be due to diluting cytosolic factors required for the action of cADPR. Moreover, since the extracellular calcium concentration is more than $10^5$ fold higher than $[Ca^{2+}]_c$, it is difficult to keep cellular calcium under low levels during these invasive manipulations. In contrast, hydrophobic derivatives of cADPR or $IP_3$ can be applied to fully intact cells, thus allowing us to test their effects on $Ca^{2+}$ release, glucose stimulated insulin secretion (GSIS), and other downstream biochemical events reliably.

Prodrug Design and Intracellular Delivery of Phosphate-containing Molecules.

Because phosphates are ionized and hydrophilic species at physiological pH, phosphate-containing molecules usually do not cross hydrophobic lipid membranes. The concept of prodrug design from pharmaceutical industry has been used to design hydrophobic derivatives of $IP_3$ and other inositol polyphosphates. Prodrug design comprises an area of drug research that is concerned with the optimization of drug delivery. A prodrug is a pharmacologically inactive derivative of a drug that requires spontaneous or enzymatic transformation within the body in order to regenerate its active parent drug molecule.

Analogues of Cyclic ADP Ribose and Their Hydrophobic Derivatives

Figure 5:
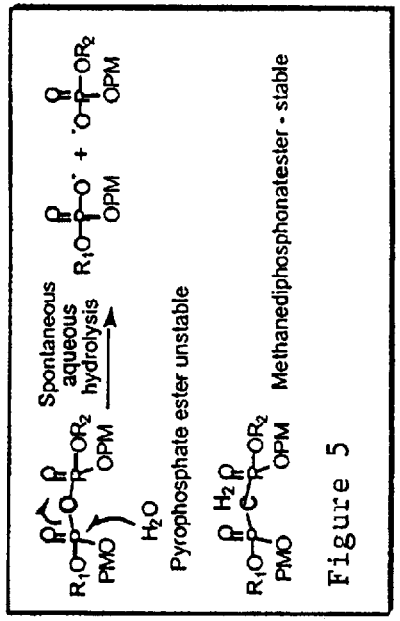
FIG. 5 depicts methanodiphosphonate alanogues of pyrophosphates and neutral esters in accordance with the present invention.

To deliver cADPR inside cells, the negative charges on the pyrophosphate must be covered. However, neutral esters of pyrophosphates are highly unstable in aqueous solutions, spontaneously breaking down into two phosphates (FIG. 5). Replacing the center oxygen atom with a methylene group forms a methanediphosphonate. The neutral esters of methanediphosphonate are stable because the center P-C bond is not susceptible to hydrolysis.

Figure 2:
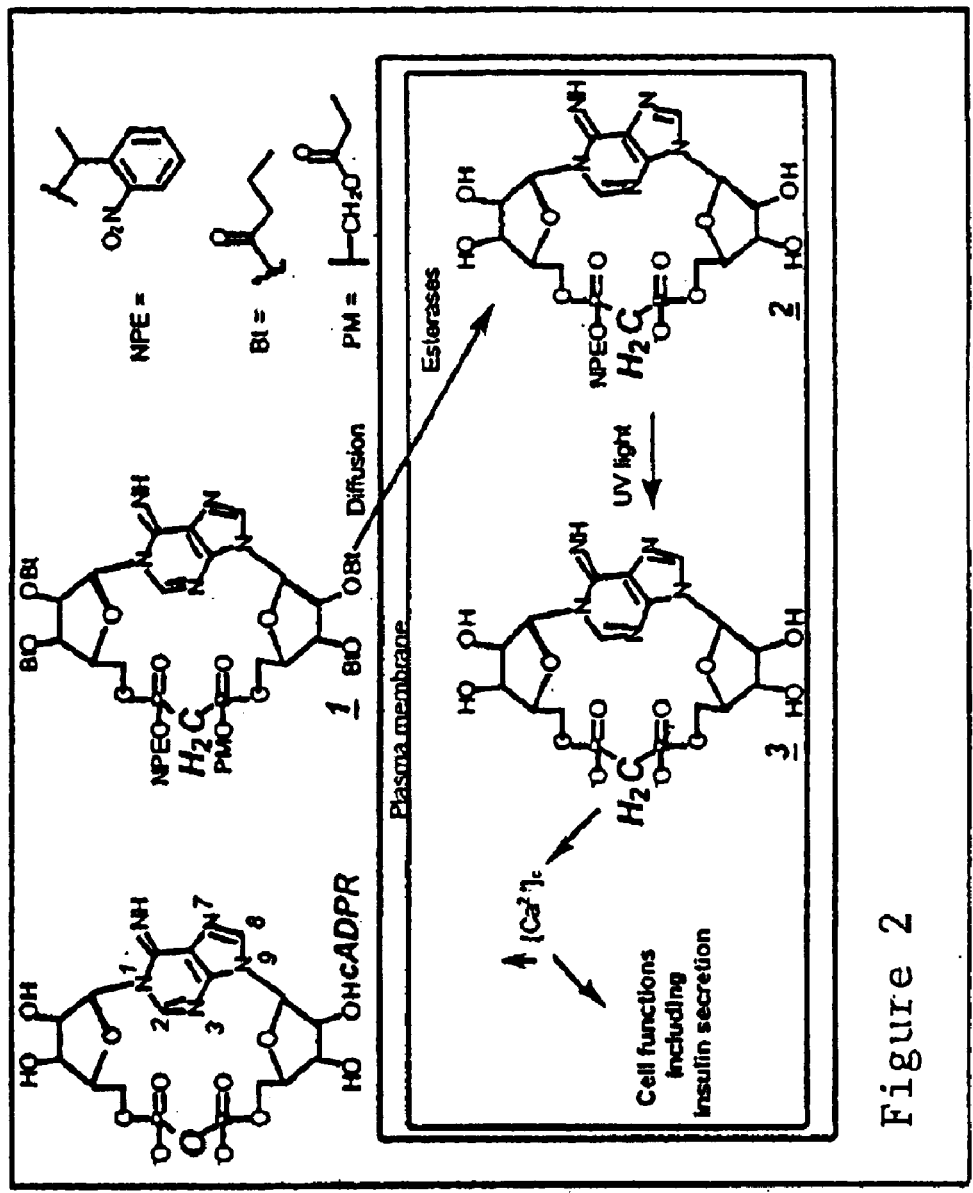
FIG. 2 depicts a pathway in accordance with the present invention.
Figure 3:
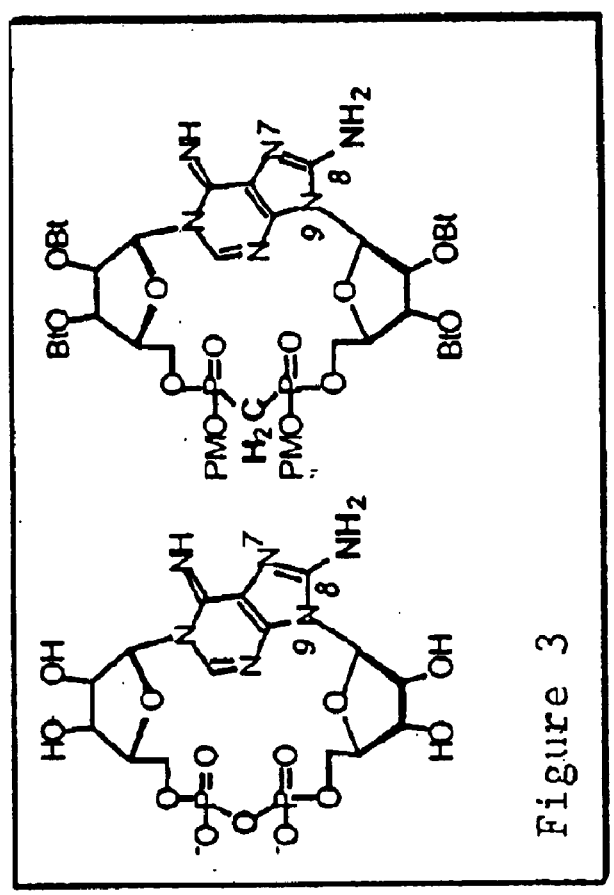
FIG. 3 depicts an 8-amino cADPR (left) and a hydrophobic derivative of cyclic ADP ribose (right) in accordance with the present invention.
Figure 4:
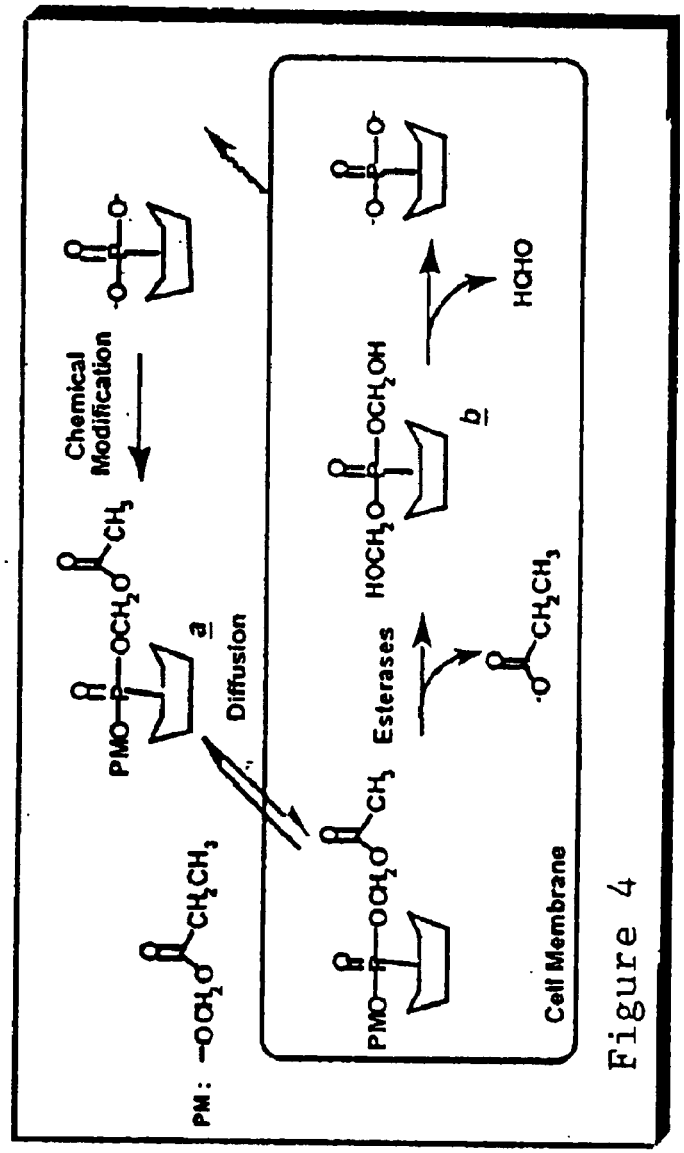
FIG. 4 depicts a pathway of the cellular delivery of phosphate- or phosphanate-containing compounds in accordance with the present invention.
Figure 6:
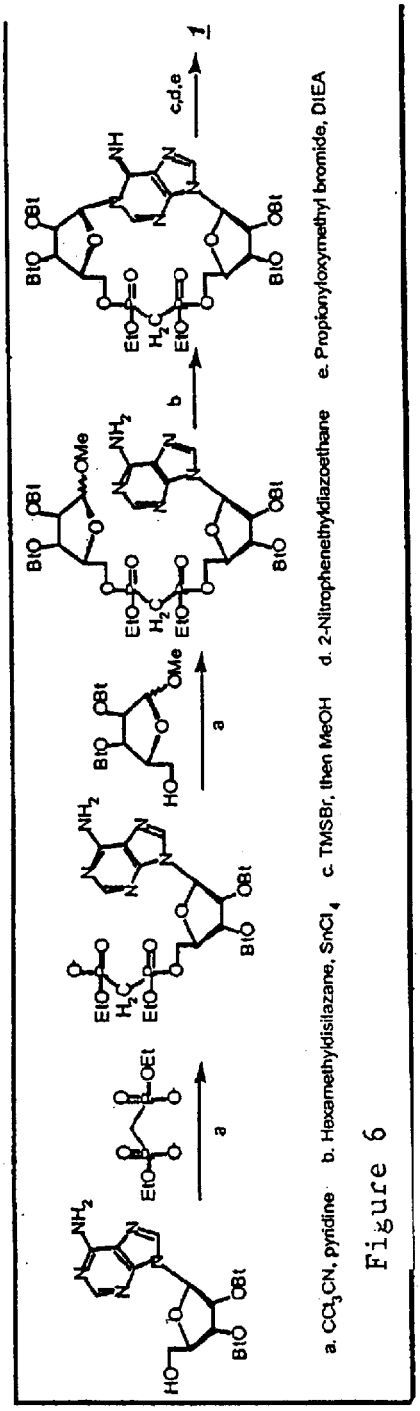
FIG. 6 depicts a synthetic scheme for preparing a photocaged and hydrophobic derivative of cyclic ADP ribose in accordance with the present invention.
Figure 7:
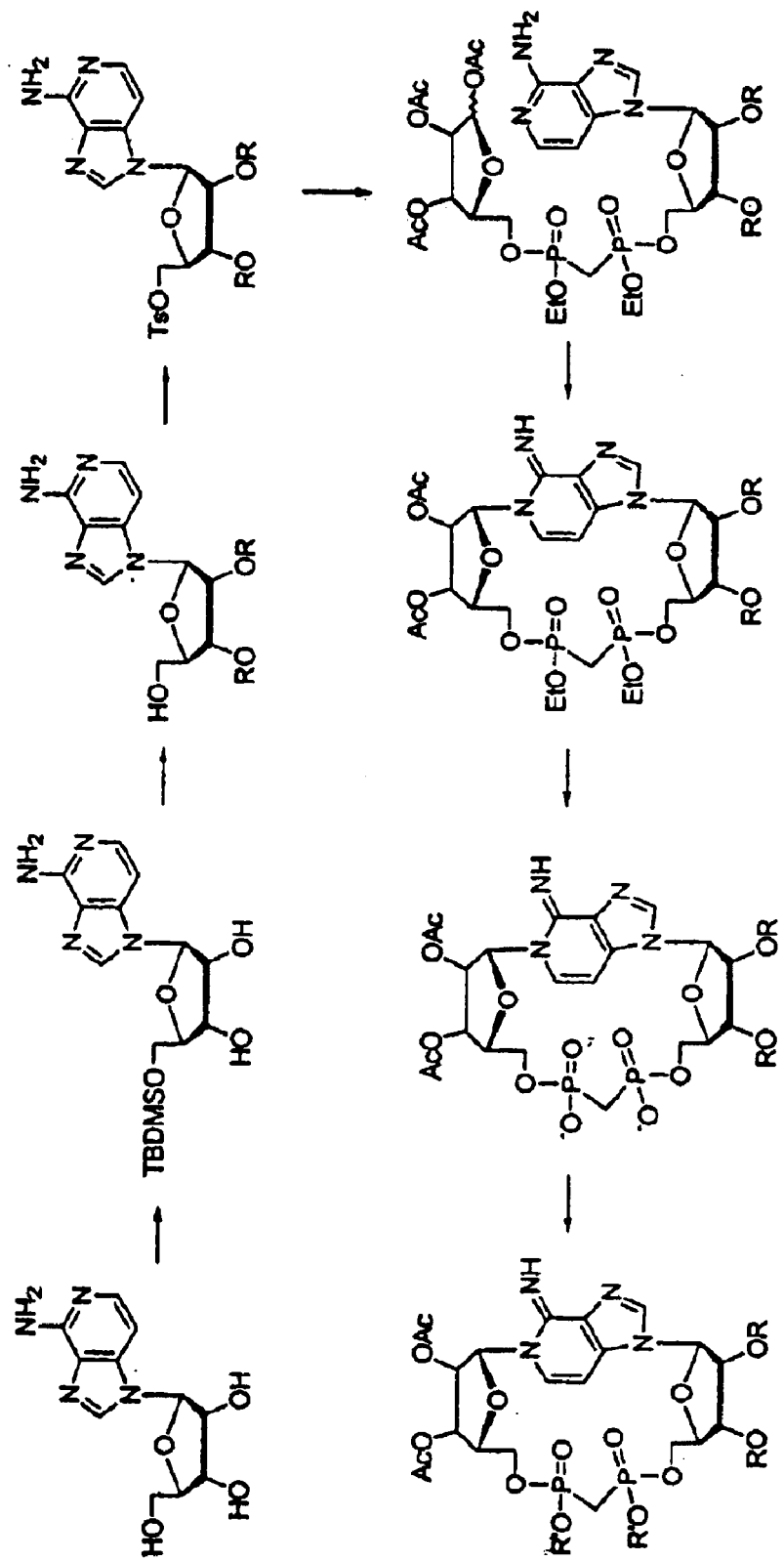
FIG. 7 depicts another synthetic scheme for preparing hydrophobic derivative of cyclic ADP ribose in accordance with the present invention.

The synthetic scheme of compound 1 (as shown in FIG. 2) is outlined in FIG. 6. Briefly, the starting material dibutyryl adenosine is coupled with the methanediphosphonate methyl ester. The resulting intermediate is coupled to another ribose derivative. Formation of the macrocycle is catalyzed TMS triflate using Hilbert-Johnson reaction to form the N1-glycosidic bond (step b in FIG. 6). After removing methyl groups with lithium cyanide (step c), the resulting methanediphosphonate is sequentially protected with one equivalent of NPE group (step d) and PM group (step e) to generate the target molecule 1. An alternative synthetic pathway for another hydrophobic derivative is shown in FIG. 7.

Figure 8:
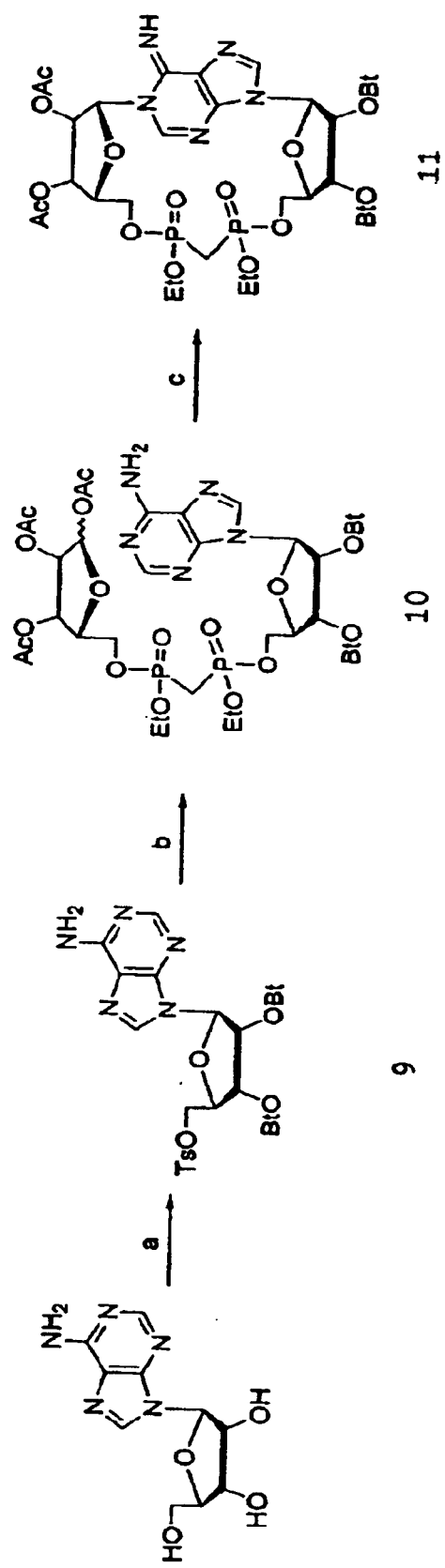
FIG. 8 depicts the synthesis of an ester of a methanediphosphonate derivative of cyclic ADP ribose.

Example of Synthesis of an Ester of a Methane-diphosphonate Derivative of Cyclic ADP Ribose The synthesis of a methane-diphosphanate derivative of cyclic ADP ribose is shown in FIG. 8. Initially, 2', 3'-dibutyryl-5'-O-tosyl adenosine (Compound 9) is prepared from adenosine in 4 steps following general procedures apparent to those of ordinary skill in the art. The structure was analyzed by $^1H$ NMR (i.e., $CDCl_3$; chemical shifts in ppm) and showed results of 0.95 (6H, m, $CH_3$), 1.6 (4H, m, $CH_2$), 2.25 (4H, m, $CH_2$), 2.4 (3H, s, $CH_3$), 4.39 (3H, m, H4' & H5'), 5.56–6.14 (3H, H3', H2' & H1'), 7.26 (2H, d, ArH, J=8.4 Hz), 7.75 (2H, d, ArH, J=8.4 Hz), 7.93 (1H, s, H2), 8.28 (1H, s, H8).

The synthetic intermediate 1,2,3-tri-O-acetyl-5-O-tosyl ribofuranose is prepared from D-ribose using the literature procedure. $^1H$ NMR results ($CDCl_3$; in ppm) are as follows: 2.04–2.11 (9H, m, $COCH_3$), 2.45 (3H, s, Ar—$CH_3$), 4.05–4.2 (3H, m, H4, H5), 5.02–5.4 (1H, m, H3), 5.31 (1H, m, H2), 6.09 (s, H1β) & 6.25 (d, J=7Hz, H1α, 1H combined), 7.36 (2H, t, ArH, J=6.3 Hz), 7.79 (2H, t, ArH, J=6.3 Hz).

The synthetic intermediate P1, P2-diethyl methane-diphosphonate bis(tetra-n-butyl ammonium) salt is prepared according to a previously reported method from the corresponding tetraethyl ester. The $^1H$ NMR results ($CDCl_3$, ppm) include: 0.84 (24H, t, $CH_3$), 1.05 (6H, m, $CH_2$), 1.31 (16H, m, $CH_2$), 1.52 (16H, m, $CH_2$), 1.91 (2H, m, P—$CH_2$—P), 3.25 (16H, m, $CH_2$), 3.87 (4H, m, $CH_2$); $^{31}P$ NMR results ($CDCl_3$): 15.99 (s).

Compound 10 or P1-5-O-(1, 2, 3-triacetyl)ribosyl P2-5'-O-(2',3'-dibutyryl)adenosyl P1,P2-diethyl methylenediphosphonate is prepared as discussed below (see FIG. 8). In brief, 2', 3'-dibutyryl-5'-O-tosyl adenosine (at least about 0.925 g, 1.65 mmol) and P1, P2-diethyl methanediphosphonate bis(tetra-n-butyl ammonium) salt (at least about 1.135 g, 1.59 mmol) are heated in DMF (1 mL) for 18 hours at 80–90 degrees Centigrade under argon. Next, 1,2,3-tri-O-acetyl-5-O-tosyl ribofuranose (0.817g, 1.9 mmol) was added to the reaction mixture and the mixture was heated for another 20 hours. After removing the solvent under vacuum, the residue was purified on a silica gel column (e.g., $CH_2Cl_2$/MeOH) to yield the unsymmetrical tetraester Compound 10 (the yield may be at least around 0.323 g or a 22% yield). Results of $^1H$ NMR($CDCl_3$, ppm) show the following: 0.8–09(6H, $CH_3$), 1.32 (6H, m, $CH_3$), 1.56 (4H, $CH_2$), 2.00 (9H, m, $COCH_3$), 2.22 (4H, $COCH_2$), 2.5 (2H, m, P—$CH_2$—P), 4.1 (4H, m, $OCH_2$), 4.38 (6H, m), 5.35 (3H, m), 5.6–5.9 (3H, m), 6.1 (1H, s), 6.2 (1H,d), 6.62 (2H, m), 8.45 (2H, m, H2 & H8); $^{31}P$ NMR ($CDCl_3$, ppm) 20.4–21.8 (m). Mass spectroscopy analysis was performed, where the mass (Electrospray, positive) that was calculated for $C_{34}H_{51}N_5O_{18}P_2$ was 880.27 ($[M+H]^+$) and found to be 880.56.

The neutral ester of a methane-diphosphonate derivative of cyclic ADP ribose or Compound 11 is prepared as follows (see FIG. 8). First, BSTFA (6 equivalents) was added to a solution of the Compound 10 (at least about 20 mg or $2.27 \times 10^{-5}$ mol) in 5 mL $CH_3CN$. TMSOTf (2 equivalents) was added subsequently and the mixture was stirred at room temperature for 6 hours. Another two equivalents of TMSOTf were then added. The reaction was quenched about two hours later by 1 mL saturated $NaHCO_3$ and extracted with dichloromethane. The organic layer was dried and purified on a silica gel column (e.g., $CH_2Cl_2$/MeOH) to give Compound 11 as analyzed by mass spectroscopy where the Electrospray, positive calculation for $C_{32}H_{47}N_5O_{16}P_2$ was 820.25 ($[M+H]^+$) and found to be 820.22.

Although this invention has been described in reference to illustrative embodiments, the description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A hydrophobic compound comprising the formula:

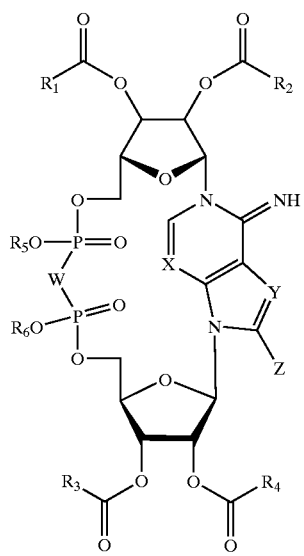

wherein, $R_1$, $R_2$, $R_3$ and $R_4$ are each independently hydrogen or linear or branched alkyl groups having from 1 to 12 carbon atoms, $R_5$ and $R_6$ are each an alkyl group, a metallic cation, a photo-labile caging group, or an acyloxymethylgroup or a homologue thereof; W is $CH_2$, $CF_2$, or CHF; X is N or CH, Y is N or CH; and Z is chosen from the group consisting of H, Br, $NH_2$, $OCH_3$, $CH_3$ and $N_3$.

2. The hydrophobic derivative recited in claim 1, wherein the photolabile caging group comprising $R_5$ and $R_6$ are independently chosen from the group consisting of:

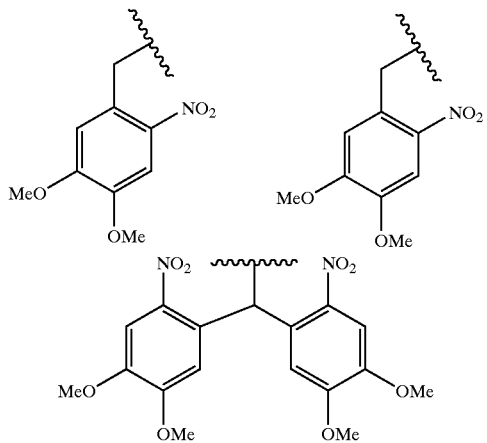

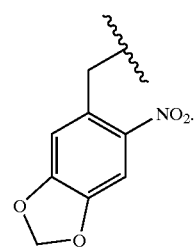

3. The hydrophobic derivative recited in claim 1, wherein the photolabile caging group comprising $R_5$ and $R_6$ are independently chosen from the group consisting of:

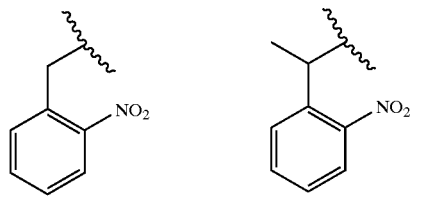

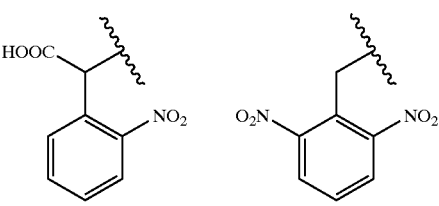

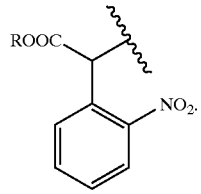

wherein R is an alkyl or aryl substituent.

4. The hydrophobic derivative recited in claim 1, wherein the photolabile caging group comprising $R_5$ and $R_6$ are independently chosen from the group consisting of:

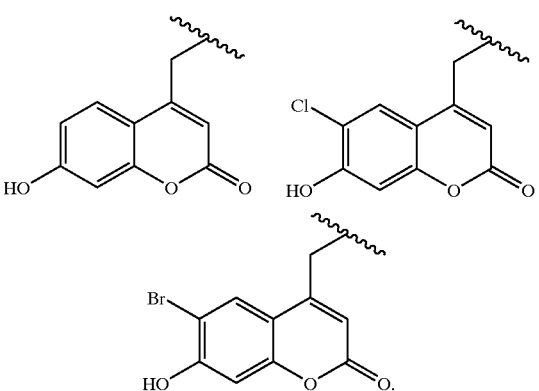

5. The hydrophobic derivative recited in claim 1, wherein $R_5$ and $R_6$ are independently chosen from the group consisting of

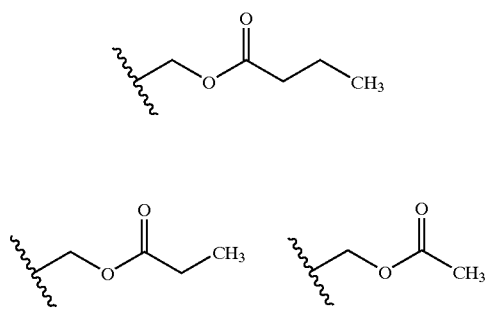

wherein the waved line indicates the point of attachment to the oxygen atoms associated with $R_5$ and $R_6$.

6. The hydrophobic derivative recited in claim 1, wherein $R_5$ and $R_6$ comprise an acyloxymethyl group or homologue at either the $R_5$ or $R_6$ position and a photolabile caging group at the other position.

7. The hydrophobic derivative recited in claim 1, wherein the photolabile caging group comprising $R_5$ and $R_6$ are independently chosen from the group consisting of:

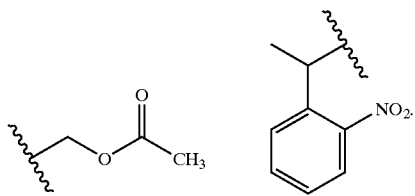

8. A method for preparing a hydrophobic composition comprising the following steps:

wherein RO and R'O comprise independently in each location carboxylate groups further comprising from 2 to 20 carbon atoms, wherein synthesis of compound 2 comprises treatment of compound 1 with tert-butyldimethylchlorosilane and imidazole in dimethylformamide, wherein synthesis of compound 3 comprises treatment of compound 2 with a carboxylic anhydride and pyridine followed by treatment with tetrabutylammonium fluoride, wherein synthesis of compound 4 comprises treatment of compound 3 with p-toluenesulfonic acid chloride and triethylamine, wherein synthesis of compound 5 comprises treatment of compound 4 with P,P'-diethyl methanephosphonate and 1,2,3-tri-O-acetyl-5-tosyl-D-ribofuranose and tributyl amine, wherein synthesis of compound 6 comprises treatment of compound 5 with N,O-bis(trimethylsilyl)trifluoro-acetamide and trimethylsilyl-p-fluorotoluenesulfonic acid in acetonitrile, wherein synthesis of compound 7 comprises treatment of compound 6 with bromotrimethylsilane followed by treatment with methanol, wherein synthesis of compound 8 comprises treatment of compound 7 with an acid halide and N,N-diisopropylethylamine in acetonitrile.

9. The method recited in claim 8, wherein the carboxylic anhydride is butyric anhydride.

10. The method recited in claim 8, wherein the 2-haloethylcarboxylate is 2-chloroethyl acetate.

11. A method for preparing a hydrophobic composition comprising the steps:

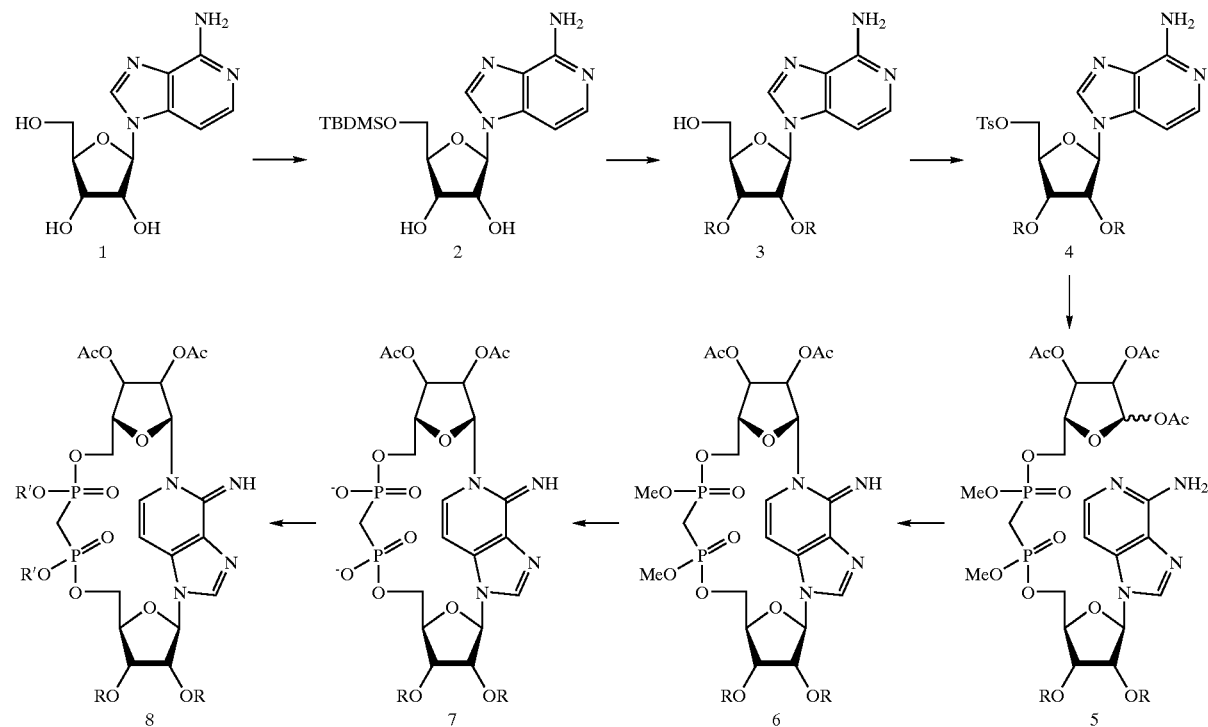

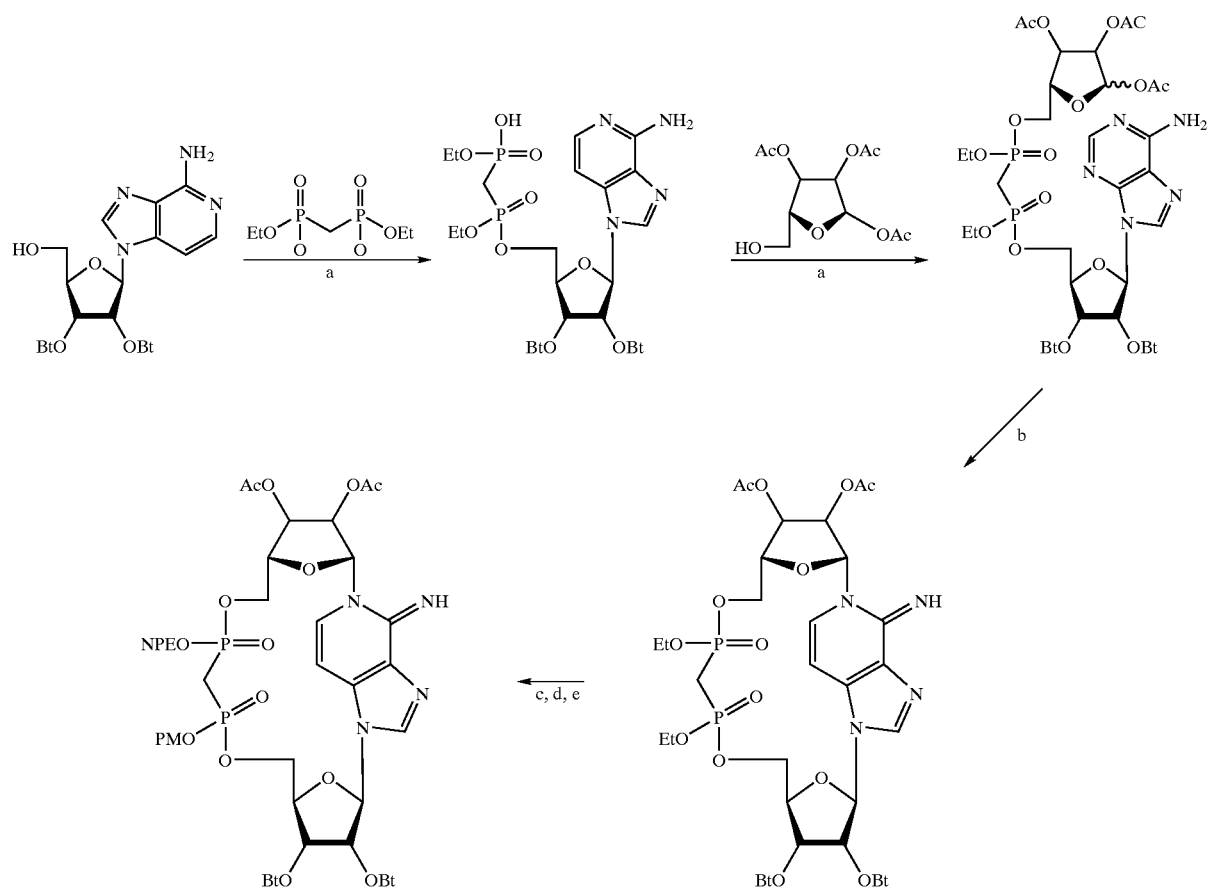
wherein:
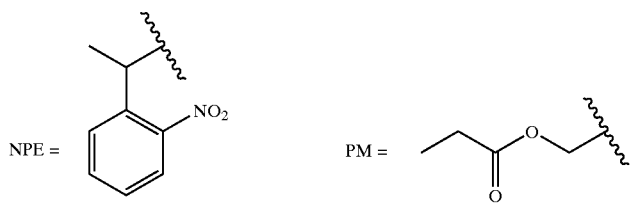
(1-(2-Nitrophenyl)ethyl group)   (Propionyloxymethyl group)
and wherein, step a includes trichloroacetonitrile and pyridine, step b includes hexamethyldisilazane and SnCl$_4$, step c includes bromotrimethylsilane then methanol, step d includes 2-nitrophenethyldiazoethane, and step e includes propionyloxymethyl bromide and a volatile amine.
* * * * *